United States Patent [19]

Swerczek

[11] Patent Number: 4,600,711
[45] Date of Patent: * Jul. 15, 1986

[54] COMPOSITION FOR TOPICAL AND INFUSION TREATMENT OF WOUNDS AND BURNS

[75] Inventor: Thomas W. Swerczek, Lexington, Ky.

[73] Assignee: The University of Kentucky Research Foundation, Lexington, Ky.

[ * ] Notice: The portion of the term of this patent subsequent to Nov. 20, 2001 has been disclaimed.

[21] Appl. No.: 660,862

[22] Filed: Oct. 15, 1984

Related U.S. Application Data

[63] Continuation-in-part of Ser. No. 409,180, Aug. 18, 1982, Pat. No. 4,483,851.

[51] Int. Cl.$^4$ ............................................. A61K 31/70
[52] U.S. Cl. ............................................................ 514/23
[58] Field of Search ........................... 424/180; 514/23

[56] References Cited

U.S. PATENT DOCUMENTS

| | | | |
|---|---|---|---|
| 327,230 | 9/1885 | Carhrick . | |
| 2,118,566 | 5/1938 | Miles | 167/96 |
| 2,139,139 | 12/1938 | Tompkins | 167/55 |
| 2,354,319 | 7/1944 | Inman | 167/96 |
| 2,826,533 | 3/1958 | Fowell | 167/74 |
| 2,895,882 | 7/1959 | Thorne et al. | 195/96 |
| 4,083,958 | 4/1978 | Bryans | 424/89 |

OTHER PUBLICATIONS

Swaney et al., *American Journal of Veterinary Research* vol. 41, Jan. 1980, pp. 127–132.
Huojnes *Theriogenology* Dec. 8, 1978.
Dabernal, *Antimicrobial Agents and Chemotherapy*, Dec. 1980, pp. 841–843.
S. P. Sahu et al., *American Journal of Veterinary Research* vol. 1, pp. 1379–1382.

*Primary Examiner*—Johnnie R. Brown
*Assistant Examiner*—Elli Peselel
*Attorney, Agent, or Firm*—Lowe, Price, Leblanc, Becker & Shur

[57] ABSTRACT

A composition is provided for the treatment of contagious equine metritis, a contagious venereal disease of horses. The composition appears to function as a biological inhibitor and has antibacterial and antifungal activity when applied to the normal flora and secretions of the epidermis and mucous membranes. Also, the composition has antipruritic and anti-inflammatory activity. The composition is efficacious in the treatment of lesions produced by bacteria, fungi, allergies, viruses, trauma, and burns to the epidermis, dermis, muscles and mucous membranes of the surface or in body cavities of animals and man.

The composition preferably comprises an aqueous solution of dextrose, citric acid and a buffering mixture of the salts of citric acid and acetic acid to provide an optional pH between 3.0 to 6.5 for various wound lesions.

21 Claims, No Drawings

COMPOSITION FOR TOPICAL AND INFUSION TREATMENT OF WOUNDS AND BURNS

CROSS REFERENCE TO RELATED APPLICATIONS

This application is a continuation in part of Ser. No. 409,180, filed Aug. 18, 1982, now U.S. Pat. No. 4,483,851.

FIELD OF THE INVENTION

This invention relates to novel compositions and their use in epidermal burns, and more particulary to novel compositions useful for the treatment of epidermal muscous membranes and muscular burns and wounds or lesions in animals and humans by topical and infusion application of the composition.

BACKGROUND

There is disclosed in my parent application, Ser. No. 409,180, filed Aug. 18, 1982, now U.S. Pat. No. 4,483,851, the disclosure of which is hereby incorporated by reference, a composition for topically relating equine metritis comprising the following formulation in water in a concentration of about 40 to 60 weight percent:

| Ingredient | Parts by Weight |
| --- | --- |
| Dextrose | 200-300 |
| Buffering Mixture | 40-110 |
| Carrier | 80-110 |

These compositions are applied topically to the external genitalia of both male and female horses affected with contagious equine metritis. In several trials the composition was found to be 100% effective in curing the diseases if used on two successive days. By comparison, antibiotics used in the prior art had to be used at least five days to be effective, and then were not 100% effective.

It has now been discovered that this and related compositions are broadly effective in treatment of *Pseudomonas aeruginosa* infected burn patients and infected skin and muscle wounds. When the composition of the invention is applied to skin burns or wounds, it provides dramatic relief of pain, and dramatically accelerates the healing process.

SUMMARY OF THE INVENTION

It is accordingly one object of the present invention to provide a novel antibacterial composition.

A further object of the invention is to provide novel compositions and methods for the treatment of bacterial and fungal infections.

A still further object of the present invention is to provide a topical composition and methods for its use in the treatment of topical conditions such as burns, blisters and infections.

An even further object of this invention is to provide a method for treating Pseudomonas infected epidermal and muscular burns and wounds.

Other objects and advantages of the present invention will become apparent to those skilled in the art as the description thereof proceeds.

In satisfaction of the foregoing objects and advantages there is provided by this invention an antibacterial and antifungal composition for the treatment of epidermal and muscular burns and wounds, which composition comprises an aqueous solution of dextrose or dextrose metabolite, a buffering mixture of weak organic acids and alkali metal salts of weak organic acids, and a carrier, the composition being characterized as a viscous solution having a pH varying from 3.0 to 6.5 depending on lesion type. Also provided by the present invention is a method for application of this composition to epidermal burns and wounds, particularly those infected with Pseudomonas, which comprises topically applying the composition to the affected area.

DETAILED DESCRIPTION OF THE INVENTION

As pointed out above, the present invention is concerned with novel compositions and a method for the treatment of epidermal burns and wounds, particularly those infected with Pseudomonas. The composition inhibits growth of the pseudomonas on the injured area, and promotes healing in burns and wounds. The composition of the present invention in its broadest embodiment comprises an aqueous solution of dextrose or dextrose metabolite, a buffering mixture of weak organic acids and/or alkali metal salts of weak organic acids, and a carrier, the solution being characterized as a relatively viscous solution having a pH ranging from about 3.0 to 6.5.

The most preferred composition may be characterized as containing the following formulation per liter of solution:

| Ingredient | Parts by Weight |
| --- | --- |
| Dextrose | 50-500 |
| Buffering Mixture | 5-200 |
| Carrier | 50-150 |

This composition also contains about 600 to 1200 parts of water, and optionally about 5 to 100 parts of an alkali metal salt of acetic acid. Preferably, the composition contains citric acid and an alkali metal salt of citric acid as important buffering components.

The dextrose component of the composition is dextrose or a dextrose metabolite which is effective to provide antibacterial and antifungal properties to the composition when used in admixture with the other components. Thus the dextrose or equivalent material is an important component in the composition.

The buffering mixture is also an important ingredient of the composition. A sufficient amount of buffer should be present to provide a resulting solution having a pH of about 3.0 to 6.5, most preferably in the range of 3.2 for antipruritic properties and 6.5 for wounds and burns. Any buffer or mixture of buffers can be used for this purpose although mixtures of weak organic acids and alkali metal salts of organic acids are especially preferred. The amount of buffering agent present is also important since the total solution should contain about 7 to 15 weight percent of buffering agent for a suitable composition.

The preferred buffering agents are polycarboxylic acids, phosphates, and the like which will provide the required pH range. The most preferred buffers, however, comprise a mixture of hydroxy polycarboxylic acids having about 3 to 8 carbon atoms and their alkali metal salts, or mixtures thereof. Preferred organic acids include citric acid, malic acid, tartronic acid, tartaric acid, and mixtures thereof as well as the sodium and potassium salts of these acids. A highly preferred buffering system comprises a mixture of citric acid and sodium citrate.

The composition optionally contains an alkali metal salt of acetic acid in an amount of about 1 to 4 parts by weight. The preferred alkali metal salt is sodium acetate, although any alkali metal salt of acetic acid may be used. The salt functions to increase the antifungal activity of the compound. This has also been shown to impart a longer shelf life to the composition. When the composition contains the alkali metal salt of acetic acid, the antifungal activity is improved so that it will not support the growth of bacteria or fungi.

It is also preferred that the resulting solution be a viscous solution to inhibit drainage from the infected organs after topical application. Thus, a carrier vehicle is included in the composition to increase the viscosity of the solution. Suitable carriers include polyalkylene glycols, methyl cellulose and the like. The preferred carrier vehicle is a lower polyalkylene glycol such as glycerine.

The carrier also provides the proper consistency to the composition so that the composition has sufficient viscosity for topical application. It also provides the necessary consistency to the solution so it can be used as a lubricant in the treatment of animals such as horses.

A preferred formulation of the invention comprises the following components per liter of solution:

| Ingredient | Parts by Weight |
| --- | --- |
| Dextrose | 50–500 |
| Hydroxy carboxylic acid | 2.5 to 100 |
| Alkali metal salt of hydroxy carboxylic acid | 2.5 to 100 |
| Carrier | 50–150 |

In a more preferred aspect of the invention, the composition would also contain an alkali metal salt of acetic acid in an amount of about 5 to 100 parts per liter of solution. Additionally, the remainder of the solution is preferably water.

The most preferred composition for use in the present invention comprises the following components:

| Ingredient | Amount |
| --- | --- |
| Dextrose | 500 grams |
| Citric acid | 100 grams |
| Sodium citrate | 50 grams |
| Glycerine | 100 cc |
| Sodium acetate | 2.5 grams |
| Distilled water | 900 cc |

The addition of sodium acetate in the most preferred embodiment increases the anti—fungal activity of the compound. The sodium acetate containing compound was shown to have longer shelf life than the same compound without sodium acetate, since it will not support the growth of bacteria or fungi.

The resulting composition is an aqueous solution with sufficient consistency to drain slowly. In use for treatment of contagious equine metritis, the composition is applied topically directly to the external genitalia of stallions and mares and preferably is used one time each day for at least two successive days. An effective amount is simply a thorough application of the viscous solution to the external genitalia manually. It has been found that this method will provide 100% effectiveness in curing horses of the contagious equine metritis organism-caused disease.

Although the composition was originally developed for treatment of contagious equine metritis, it has been found that the composition is also effective against Pseudomonas infections where the infection occurred on the external genitalia of the affected horses. This discovery led to the discovery of use of the composition of the invention for burn patients and patients with skin and muscle wounds infected with Pseudomonas bacterias, particularly *Pseudomonas aeruginosa*. When the composition was applied to accidental skin burns, it not only gave dramatic relief of pain, but also prevented the blistering of the epidermis as well as dramatically accelerating wound healing. The same results were obtained in several cases with skin burns from sun, steam, heat, friction and grease.

The compound was also shown to accelerate the healing of contact (allergenic) dermatitis. When the compound was applied at the time of exposure to poison ivy, the skin lesions of poison ivy did not develop. When applied to early cases, the compound was shown to be antipruritic within a few minutes of application, and greatly accelerated the healing of the skin lesions. Similar relief and reduction of swelling was observed in cases of insect-induced skin reactions. The composition is also useful in healing burns caused by friction, chemical and heat.

In experiments involving skin and wound lesions of dogs, cats, cattle and horses, the composition of the invention was shown to greatly accelerate the healing of superficial and deep skin and muscle wounds. It not only prevented bacterial and fungal infections of the wound, but it dramatically hastened the healing of the wound and the new growth of skin thereover. In numerous cases of animal wounds involving cats, dogs, cattle and horses, the composition dramatically promoted complete wound healing after other "state of the art" medical treatments failed to produce satisfactory results.

Although the exact mechanism by which the composition works is not known, it was originally developed to enhance the normal bacteria flora of the skin to produce an anti-bacterial-like metabolite to inhibit the growth of the contagious equine metritis (CEM) organism. In addition to the production of the antibacterial metabolite, it appears that the rapid healing of wounds caused by the composition of the invention provides an environment that discourages the growth of pathogenic bacteria and fungi.

Further, the composition has other beneficial properties and functions, including anti-pruritic properties, reduction of tissue fluids in epidermal vesicles and wound lesions, increased circulation to wound lesions and inhibition of bacterial and fungal growth in wounds.

In preliminary tests on numerous cases of burns and naturally induced viral, bacterial, fungal, allergic and traumatic diseases of the eye, external ear, nose, oral mucosa, periodontal tissues, external genitalia, vagina, uterus, perianal and dermal tissue, and muscles affected with deep wound lesions, the composition was shown to dramatically accelerate the healing of lesions in the mucous membranes, epidermis, dermis and muscles. With the exception of neoplasia, the compound was effective on any type of lesion.

The following examples are to illustrate the invention, but the invention is not to be considered as limited thereto. In the examples and throughout the specification, parts are by weight unless otherwise indicated.

EXAMPLE 1

The following composition was prepared:

| Ingredient | Parts by Weight |
|---|---|
| Dextrose | 250 grams |
| Citric acid | 50 grams |
| Sodium citrate | 25 grams |
| Glycerine | 100 ccs. |
| Water | 400 ccs. |

The resulting composition was a viscous solution having a pH of 3.20.

To show the effectiveness of the compound on CEM, twenty horses were selected for testing. Each of the twenty horses was treated with a single treatment of the solution by manually applying topically directly to the external genitalia of the horses. From this test, 17 of the horses were found to be cured by the single treatment. The three horses which were not cured with the single treatment were then treated again with two successive treatments which were found to successfully cure the disease. Accordingly, in the field it is recommended that the disease be treated one time per day with application of the composition on at least two successive days.

EXAMPLE 2

The following composition is prepared:

| Ingredient | Parts by Weight |
|---|---|
| Distilled water | 900 cc. |
| Glycerine | 100 cc. |
| Dextrose | 500 grams |
| Citric acid | 100 grams |
| Sodium citrate | 50 grams |
| Sodium acetate | 2.5 grams |

The resulting composition is a viscous solution having a pH of 3.0. The compound of the invention is topically applied to ten patients having second degree epidermal heat burns. In all ten cases, the patients experience dramatic relief of pain, and no blistering of the burn area occurs. Further, the healing time of the burn is dramatically accelerated. In addition, none of the patients develop *Pseudomonas aeruginosa* infections in the area of the burn. Similar results are obtained in cases where the skin burns are caused from sun, steam, friction and grease.

The invention has been described herein with reference to certain preferred embodiments. However, as obvious variations thereon will become apparent to those skilled in the art, the invention is not to be considered as limited thereto.

I claim:

1. A composition for the treatment of bacterial infections which comprises dextrose in an aqueous based mixture including a buffer present in sufficient amounts to provide a pH in the range of from 3.0 to 6.5, and a carrier; said composition comprising the following: 50 to 500 parts by weight of dextrose, 5 to 200 parts by weight of buffer comprising a mixture of hydroxy carboxylic acids and alkali metal salts of hydroxy carboxylic acids, 50 to 150 parts by weight of a carrier to increase viscosity of the composition, and about 5 to 100 parts by weight of an alkali metal salt of acetic acid.

2. A composition for the treatment of fungal infections which comprises dextrose in an aqueous based mixture including a buffer present in sufficient amounts to provide a pH in the range of from 3.0 to 6.5, and a carrier; said composition comprising the following: 50 to 500 parts by weight of dextrose, 5 to 200 parts by weight of buffer comprising a mixture of hydroxy carboxylic acids and alkali metal salts of hydroxy carboxylic acids, 50 to 150 parts by weight of a carrier to increase viscosity of the composition, and about 5 to 100 parts be weight of an alkali metal salt of acetic acid.

3. A composition according to claim 2 which comprises about 50 to 500 parts of dextrose, about 25 to 100 parts of a hydroxy carboxylic acid, about 2.5 to 100 parts of an alkali metal salt of a hydroxy carboxylic acid, and about 50 to 150 parts of a polyalkylene glycol carrier.

4. A composition according to claim 1 wherein the bacterial infection is a Psuedomonas infection.

5. A composition according to claim 1 or 2 wherein the components of the composition are contained in a 40–60 weight percent concentration in water.

6. A composition according to claim 1 which comprises about 50 to 500 parts of dextrose, about 25 to 100 parts of a hydroxy carboxylic acid, about 2.5 to 100 parts of an alkali metal salt of a hydroxy carboxylic acid, and about 50–150 parts of a carrier.

7. A composition according to claim 6 or 3 wherein the hydroxy polycarboxylic acid component is selected from the group consisting of citric acid, tartronic acid, malic acid, tartaric acid, and mixtures thereof.

8. A composition according to claim 6 or 3 wherein the alkali metal salt of the hydroxy polycarboxylic acid is selected from the group consisting of sodium and potassium salts of citric acid, tartronic acid, malic acid, tartaric acid, and mixtures thereof.

9. A composition according to claim 6 or 3 wherein the carrier is a polyalkylene glycol.

10. A composition according to claim 1 or 2 which comprises 250 parts dextrose, 50 parts citric acid, 25 parts sodium citrate, 100 ccs. glycerine and 400 ccs. water, said composition being in the form of a viscous solution having a pH in the range of 3.2.

11. A composition according to claim 1 or 2 comprising:

| Ingredient | Parts by Weight |
|---|---|
| Dextrose | 500 grams |
| Citric acid | 100 grams |
| Sodium citrate | 50 grams |
| Glycerine | 100 cc |
| Sodium acetate | 2.5 grams |
| Distilled water | 900 cc |

12. A method for the treatment of epidermal and muscular burns which comprises topical application of an effective amount to the burn area of an aqueous based mixture of dextrose, a buffer present in sufficient amounts to provide a pH in the range of about 3.0 to 4.5 and a carrier.

13. A method for the treatment of epidermal and muscular wounds which comprises topical application of an effective amount to the wound area of an aqueous based mixture of dextrose, a buffer present in sufficient amounts to provide a pH in the range of about 3.0 to 4.5 and a carrier.

14. A method according to claim 12 or 13 where the components of the composition are contained in a 40–60 weight percent concentration in water and are present in the following amounts by weight:

| Ingredient | Parts by Weight |
|---|---|
| Dextrose | 50–500 grams |
| Buffer | 5–200 grams |
| Carrier | 50–500 grams |

15. A method according to claim 12 or 13 wherein the composition comprises about 50–500 parts of dextrose, about 2.5–100 parts of hydroxy carboxylic acid, about 2.5–100 parts of an alkali metal salt of a hydroxy carboxylic acid, and about 50–150 parts of a carrier.

16. A method according to claim 12 or 13 wherein the hydroxy polycarboxylic acid component is selected from the group consisting of citric acid, tartronic acid, malic acid, tartaric acid, and mixtures thereof.

17. A method according to claim 12 or 13 wherein the alkali metal salt of the hydroxy polycarboxylic acid is selected from the group consisting of sodium and potassium salts of citric acid, tartronic acid, malic acid, tartaric acid, and mixtures thereof.

18. A method according to claim 12 or 13 wherein the carrier is a polyalkylene glycol.

19. A method according to claim 12 or 13 wherein the composition additionally comprises an alkali metal salt of acetic acid.

20. A method according to claim 12 or 13 wherein the burn or wound site is infected with Pseudomonas.

21. A method for the treatment of contact dermatitis which comprises applying the composition of claim 1 or 2 topically to the site of the contact dermatitis.

* * * * *